(12) United States Patent
Walker et al.

(10) Patent No.: US 6,802,812 B1
(45) Date of Patent: Oct. 12, 2004

(54) NONINVASIVE OPTICAL SENSOR FOR MEASURING NEAR INFRARED LIGHT ABSORBING ANALYTES

(75) Inventors: Stephen D. Walker, Boulder, CO (US); John E. Repine, Englewood, CO (US); Charles W. Henry, Denver, CO (US); Harry L. Valenta, Jr., Aurora, CO (US); Peter E. Nelson, Longmont, CO (US); R. Dale Zellers, Lafayette, CO (US)

(73) Assignee: Nostix LLC, Boulder, CO (US)

( * ) Notice: Subject to any disclaimer, the term of this patent is extended or adjusted under 35 U.S.C. 154(b) by 451 days.

(21) Appl. No.: 09/917,414

(22) Filed: Jul. 27, 2001

(51) Int. Cl.[7] .................................................. A61B 5/00
(52) U.S. Cl. ........................................ 600/309; 600/323
(58) Field of Search .............................. 600/309, 310, 600/320, 321, 322, 327, 328, 300–436; 435/4, 5, 6, 808; 250/493.1, 495.1, 338.1, 338.4, 340, 363.01; 356/39, 40, 41, 42

(56) References Cited

U.S. PATENT DOCUMENTS

| | | | | |
|---|---|---|---|---|
| 4,805,623 A | * | 2/1989 | Jobsis | 600/328 |
| 5,198,667 A | * | 3/1993 | Glembocki et al. | 250/306 |
| 5,433,197 A | * | 7/1995 | Stark | 600/319 |
| 5,943,158 A | * | 8/1999 | Ford et al. | 359/295 |
| 6,222,189 B1 | * | 4/2001 | Misner et al. | 250/341.1 |
| 6,411,833 B1 | * | 6/2002 | Baker et al. | 600/336 |
| 6,453,183 B1 | * | 9/2002 | Walker | 600/322 |
| 6,483,791 B1 | * | 11/2002 | Asada et al. | 369/59.11 |
| 6,580,934 B1 | * | 6/2003 | Braig et al. | 600/310 |
| 6,661,562 B2 | * | 12/2003 | Walker | 359/295 |
| 6,675,031 B1 | * | 1/2004 | Porges et al. | 600/322 |

* cited by examiner

Primary Examiner—Daniel Robinson
(74) Attorney, Agent, or Firm—Koestner Bertani LLP; Ken J. Koestner

(57) ABSTRACT

An optical sensor includes an optical source capable of being positioned on a tissue and emitting near infrared light into the tissue at a plurality of selected wavelengths, and a photodetector capable of detecting reflected light from the tissue. The photodetector being positioned on the tissue removed from the optical source but sufficiently close in proximity to the optical source to contact the same general tissue. The optical sensor further includes an oscillator coupled to the optical source and capable of activating the optical source to emit the near infrared light, and a modulator coupled to the oscillator and capable of controlling radio frequency modulation of the optical source to emit a radio frequency component that is used to measure the optical path length and absorbance of an analyte of interest within the tissue.

35 Claims, 2 Drawing Sheets

NONINVASIVE OPTICAL SENSOR FOR MEASURING NEAR INFRARED LIGHT ABSORBING ANALYTES

BACKGROUND OF THE INVENTION

Measurement of the concentration of light absorbing analytes in human tissue has many clinical uses. For example, cerebral oxygenation can be determined by analyzing concentrations of oxyhemoglobin and deoxyhemoglobin in the brain. Cerebral oxygenation measurements have wide clinical usage including monitoring of high risk pregnancy, premature infants, monitoring of psychological or neurological condition of a patient, monitoring of cognitive state, and others.

One device for measuring the concentration of light absorbing analytes in human tissue is pulse oximetry. Pulse oximeters measure hemoglobin saturation, the ratio of oxygen actually carried by hemoglobin to the oxygen-carrying capacity of hemoglobin. Pulse oximeter saturation readings are useful as a noninvasive, continuous alternative to blood samples. One example of a pulse oximeter with multiple optical sources is disclosed in U.S. Pat. No. 5,902,235, entitled "Optical cerebral oximeter" and issued to Lewis. The pulse oximeter disclosed by Lewis has light-emitting diodes (LED) that produce two different wavelengths of light, 660 nm and 890–950 nm, and a common detector.

Pulse oximeters have several disadvantages. For example, pulse oximeters are not capable of measuring path length so short path lengths of less than 1 cm, typically through the finger or earlobe, are used for measurement. Tissue is alternately irradiated by the two LED sources and absorbance is measured on a "pulse", the systolic portion of the heartbeat. The ratio of the two absorbances is multiplied by an experimentally obtained constant to determine saturation. Pulse oximeters generally have an experimentally determined table stored in memory that relates the ratio of the two absorbances to blood oxygen saturation.

Pulse oximeters can be used to detect fetal hypoxia. Hypoxia occurs when the oxygen supply to the brain is inadequate for normal cellular function. Hypoxia can result in brain damage and/or death of the fetus. Fetal hypoxia can result in the uterus if the umbilical cord wraps around a fetus' neck, thereby restricting blood flow to the head. A high-risk fetus typically lacks cerebral blood pressure regulation mechanisms that are found in adults and normal fetuses. Contractions can cause cerebral hemorrhage that leads to hypoxia in high-risk fetuses.

Current technology includes two instruments that attempt to detect fetal hypoxia. Neither instrument produces reliable measurements. A first instrument is a Doppler ultrasound instrument that records the fetal heartbeat through the mother's abdominal wall. Cardiac accelerations and decelerations on the recording are visually analyzed to determine whether the fetus is in a distress condition. A practitioner using a Doppler ultrasound instrument frequently fails to detect actual hypoxia and falsely detects the hypoxia condition when not present because the parameter sensed is fetal heartbeat rather than the more-efficacious parameter of fetal cerebral oxygenation. A second instrument is a pulse oximeter that is inserted into the uterus in contact with the fetal cheek. Pulse oximeters are inaccurate at common fetal saturation levels in the range from 35% to 50%.

Cerebral blood flow (CBF) is the amount of blood passing a volume of brain tissue. One system for measuring cerebral blood flow is described in U.S. Pat. No. 5,251,632, entitled "Tissue oxygenation measurement system", and issued to Delpy. Delpy describes a system that uses near infrared spectrophotometry in combination with pulse oximetry to measure cerebral blood flow. The Delpy system has several components including a near infrared spectrophotometer and a pulse oximeter, in addition to a computer, a mixer, and a ventilator. The Delpy system uses the ventilator and mixer to generate a 5–10% step change in inspired oxygen and measures the change of oxyhemoglobin ($HbO_2$) concentration induced by the oxygen infusion. The oxygen step is used as a tracer in the Fick method of determining flow. The computer calculates cerebral blood flow by dividing the rate of accumulation (dQ/dt) of oxyhemoglobin by the difference between the arrival rate and the departure rate of oxyhemoglobin. The amount of oxyhemoglobin in cerebral tissue is measured by the near infrared spectrophotometry. The difference between oxygen arrival and departure rate is the saturation of blood in the infant earlobe as measured by the pulse oximeter.

The Delpy technique for measuring cerebral blood flow has several disadvantages. The technique suffers from inaccuracies due to the measurement of Hb and $HbO_2$ at different parts of the body and using different measurement methods. Multiple devices, including multiple sensors, a ventilator, a mixer, and a computer, must operate in cooperation with precise timing, introducing the possibility of error for each device. The Delpy technique has high complexity, requiring synchronization of multiple different medical devices with a computer. The Delpy system cannot be operated without specially trained staff and software, increasing complexity and cost. In addition, the Delpy technique introduces risk in varying the inspired oxygen concentration of critically ill pre-term infants and can only be used on patients who are mechanically ventilated.

Another clinical use of light-absorbing analyte measurement is diagnosis of acute lung injury involving any form of acute respiratory insufficiency. U.S. Pat. No. 5,679,532, entitled "Serum Ferritin as a Predictor of the Acute Respiratory Distress Syndrome (ARDS)," and issued to Repine, describes a method for determining the potential to develop ARDS, a severe subset of acute lung injury, in an at-risk patient. Repine discloses a technique for determining the patient's serum concentration of ferritin in a blood sample and determining ARDS development potential from the serum concentration of ferritin. The disadvantage of the Repine system is that a blood sample must be taken.

Another clinical use of light-absorbing analyte measurement is determination of arterial blood gas concentrations. An arterial blood sample is drawn from the patient and parameters having clinical value are measured with laboratory instruments including pH, and the partial pressure of oxygen and the partial pressure of carbon dioxide. Clinicians use arterial blood gas measurements to adjust inspired oxygen concentration and respiratory rate of ventilated patients to assure adequate tissue oxygenation.

SUMMARY OF THE INVENTION

Near infrared spectrophotometry noninvasively and accurately measures the concentration of light absorbing analytes in human tissue.

In accordance with aspects of the present invention, an optical sensor includes an optical source capable of being positioned on a tissue and emitting near infrared light into the tissue at a plurality of selected wavelengths, and a photodetector capable of detecting reflected light from the tissue. The photodetector is positioned on the tissue removed from the optical source but sufficiently close in proximity to the optical source to contact the same general tissue. A high frequency oscillator is directly coupled to the source. The sensor is coupled to a radio frequency (RF) signal processor that is capable of detecting baseband modulation components from an RF carrier which makes use of the high frequency source oscillator. Examples of RF signal processors are direct conversion receivers, tuned RF receivers, superheterodyne receivers with either synthesized or variable frequency reference oscillators, and the like. The magnitude and phase of the baseband detector furnishes an estimate of the optical path length as well as the absorption. In addition, the source may be wavelength modulated by current control and/or by temperature cooler and a power supply to generate close-proximity optical wavelengths. The wavelength modulation shift in conjunction with additional baseband signal processing provides additional normalization to reduce scattering errors.

In accordance with aspects of the present invention, an apparatus includes (a) a single optical source capable of emitting near infrared light into the tissue at a plurality of selected wavelengths, (b) a detector capable of detecting reflected light in response to emission by the optical source, (c) a signal activator coupled to the optical source and capable of activating and modulating the optical source emitting the selected wavelengths in a range of wavelengths within one percent of a first nominal wavelength, and (d) an analyzer coupled to the detector and capable of analyzing changes in modulation intensity and phase between light emitted into the tissue and light reflected from the tissue to determine $\mu_a$, the absorbance of the tissue, according to equation:

$$\mu_a = \frac{\ln 10}{-2c} \left( \frac{\frac{dA}{d\mu_a}}{\frac{d\theta}{d\mu_a}} \right) = \frac{\ln 10}{-2c} \left( \frac{\Delta A}{\Delta \theta} \right)$$

where $dA/d\mu_a$ is modulation amplitude difference and $d\theta/d\mu_a$ is the modulation phase difference between two slightly shifted wavelengths in the selected range of wavelengths, and c is the speed of light.

Further in accordance with various aspects of the invention, the signal activator is capable of activating and modulating the optical source to emit the selected wavelengths in a range of wavelengths within one percent of the first nominal wavelength, emit the selected wavelengths in a range of wavelengths within one percent of a second nominal wavelength, and emit the selected wavelengths in a range of wavelengths within one percent of a third nominal wavelength.

In accordance with other aspects of the invention, a method of sensing a parameter includes emitting near infrared light into the tissue at a plurality of selected wavelengths, and detecting reflected light from the tissue at a distance removed from the emission but sufficiently close in proximity to contact a same general tissue. The method further includes activating emission of the near infrared light to emit a plurality of wavelengths that are selected to increase amplitude and slope of absorbency of a compound of interest within the tissue.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENT(S)

Near infrared spectrophotometry measurements are used in medical, biological, and physiological devices to measure the concentration of light-absorbing analytes in human tissue.

Figure 1:
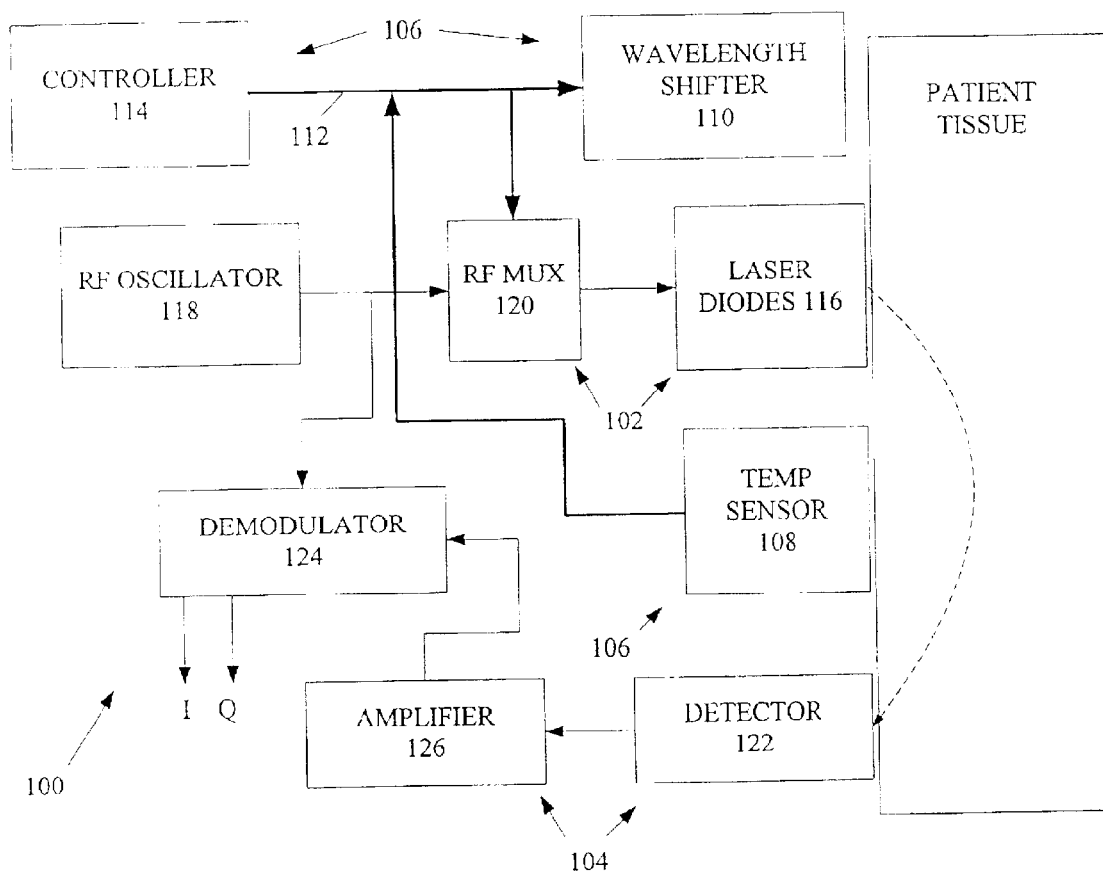
FIG. 1 depicts a schematic block diagram showing a near infrared spectrophotometer in accordance with an embodiment of the present invention.

Referring to FIG. 1, a schematic time diagram illustrates an example of a near infrared spectrophotometer 100. Fundamental elements of the near infrared spectrophotometer 100 are an optical radiation source 102 and a detector 104 for detecting radiation produced by the optical source 102. The illustrative near infrared spectrophotometer 100 has a single optical source 102 and a single detector 104 although additional sources and detectors may be utilized in other systems.

The near infrared spectrophotometer 100 also includes a temperature control system 106 including a temperature sensor 108 and a wavelength shifter 110. The near infrared spectrophotometer 100 has control interconnections 112 for controlling the optical source 102 and the temperature control system 106. The control interconnections 112 supply control signals from a controller 114 to the optical source 102 and wavelength shifter 110, and receive control signals from the temperature sensor 108. In various embodiments, the controller 114 may be implemented in different forms such as a processor, a CPU, a microcontroller, a digital signal processor (DSP), logic circuits, programmable logic arrays, and the like. Some examples of the near infrared spectrophotometer 100 may include an internal controller 114 so that the control interconnections 112 may be a control line, a bus, or other internal interconnect. Other systems may have an external control system so that the control interconnections 112 may include an interface such as a serial interface, a parallel interface, an external bus interface or the like.

The controller 114, whether internal or external, may include other interconnections for interfacing to external devices, for example infusion pumps, electrophysiologic control devices, ventilators, and many other diagnostic and therapeutic devices. The near infrared spectrophotometer 100 may be used in combination with other clinical and laboratory techniques using the interface or without interfacing to improve the diagnosis, treatment, or prevention of a pathophysiologic condition.

The near infrared spectrophotometer 100 can utilize the controller 114 to monitor physiologic function of a patient. The controller 114 can execute processes that monitor physiologic parameters for early recognition of a condition and, upon detection of the condition, rapidly supply a suitable treatment for various conditions. For example, monitoring of a condition can be used to reduce automated administration of drugs to meet the patient's needs. Monitoring can be used to automatically reduce automated inspired oxygen levels to minimal levels of effective oxygenation for ventilated patients, reducing problems related to toxicity of excessive concentrations of oxygen.

In an illustrative system, the optical source 102 utilizes laser diodes 116 to generate optical radiation. The laser diodes 116 are activated by electrical signals from a RF oscillator 118 as controlled by an RF multiplexer 120. Other types of optical sources may be utilized in other embodiments. Suitable optical sources include vertical cavity surface emitting lasers (VCSEL), edge-emitting laser diodes, distributed feedback lasers (DFB), and the like. Typically a single optical source 102 is used although some systems may utilize multiple optical sources.

The detector 104 includes an optical detector 122 that detects optical signals and applies the optical signals to a demodulator 124. An amplifier 126 is positioned between the optical detector 122 and the demodulator 124 to amplify the signals. One example of a suitable amplifier 126 is a preamplifier followed in series by a radio frequency amplifier.

The demodulator 124 produces In-Phase (I) and Quadrature (Q) measures of the detected signal. The RF oscillator 118 applies electrical signals to the demodulator 124.

The optical source 102 has several design characteristics that enhance the measurement of small absorbances and short path lengths in tissue. The optical source 102 generates infrared energy that irradiates tissue at wavelengths chosen to minimize water interference and to maximize the absorbance of a compound of interest. The entering wavelengths are further specified to be in a spectral region in which slight changes in wavelength produce significant changes in absorbance level of the analyte of interest. For example, 760 nm to 765 nm is an optical wavelength range for measuring absorption of oxyhemoglobin and deoxyhemoglobin as the compounds of interest. When the wavelength is shifted slightly from 760 nm to 765 nm the change in absorbance is significant.

The detector 104 has aspects that are exploited to accurately measure path length in tissue. The demodulator 124, amplifier 126, and optical detector 122 of the detector 104 are operated to accurately measure pathlength on the basis of modulation phase and amplitude shift measurements. Modulation phase shift increases with increasing path length and provides the basis for path length measurement.

The controller 114 controls the optical radiation source 102 and detector 104 to shift the incident wavelength to reduce or eliminate scattering error. The controller 114 controls the RF multiplexer 120 in the signal pathway from RF oscillator 118 to the laser diodes 116 to use wavelength shifting on the order of 2–5 nm to reduce scattering error. The near infrared spectrophotometer 100 acquires two measurements with an identical optical path. The light loss due to scattering is constant, the same in both measurements, so that a change in reflected light is mainly caused by absorbance of the selected analyte of interest.

In an illustrative embodiment, the radio frequency (RF) multiplexer 120, VCSEL laser diodes 116, and wavelength shifter 110 are controlled through a digital port of controller 114, an embedded microcomputer. In one example, the laser diodes 116 are configured as two ten-element VCSEL arrays. Each VCSEL array element emits 1 mW to produce a total of 10 mW when all ten elements activated. The 10 mW value is ten percent of the recognized laser damage threshold of 100 mW. The controller 114 also monitors skin temperature with the temperature sensor 108 positioned in close proximity to the VCSELs of laser diodes 116. If skin temperature exceeds a predetermined threshold, the VCSELs are immediately inactivated.

In one example, the RF oscillator 118 generates a 145 MHz signal for both modulation and demodulation. RF multiplexer 120 sequentially applies radio frequency modulation to each VCSEL in the laser diodes 116 so that only a single VCSEL is activated at any time.

The emitted wavelength is shifted either longer or shorter by the wavelength shifter 110. One or more of several possible techniques are used to shift wavelengths. One technique is to vary input current to the source. An increase in current lengthens the wavelength. Another technique is to control optical source temperature with a thermoelectric cooler. Higher temperatures result in longer wavelengths. Cooler temperatures produce shorter wavelengths. A third technique is to attach a tunable external cavity to the optical source.

Another class of techniques involves usage of micro-electro-mechanical systems (MEMS) forming a portion of the optical source to vary wavelength of the optical source. Optical MEMS products, which may be called micro-optico-electro-mechanical systems (MOEMS) typically operate by manipulating tiny mirrors within the optical source. Individuals having ordinary skill in the MEMS art are familiar with MEMS chips that use light beam-directing mirrors that move independently and nearly instantaneously during operation. A MEMS optical source can be arranged into pixels in which a pixel can be activated by directing a mirror at a projection lens and be deactivated by directing the mirror away from the projection lens.

Other suitable techniques for shifting wavelength that are known to one having ordinary skill in the art may also be used.

The wavelength shifter 110 first shifts the emitted wavelength to long values and In-Phase (I) and Quadrature (Q) results are measured. The wavelength shifter 110 then lowers the emitted wavelength to short values, and measurements are repeated. The measurements produce In-Phase (I) and Quadrature (Q) results that the controller 114 users to calculate modulation amplitude difference $dA/d\mu_a$ and phase difference $d\theta/d\mu_a$.

An optimum pathlength generates about a 10 degree phase change in the measurement, approximately 0.2 nsec corresponding to about 60 mm for a 145 MHz source signal.

In one example, the optical detector 122 is an avalanche photo diode. A source/detector separation of 4 cm gives a mean penetration of 2 cm and a tissue volume of approximately 5 ml.

Typically, measurements can be made at a patient's bedside. A clinician places the optical source 102 and photodetector 104 over a body region of the patient at which measurements are desired. Near infrared light penetrates several centimeters into the tissue. A portion of the light is reflected back to the photodetector 104 on the skin. Wavelengths of the entering light are selected to emphasize the light absorbing compounds of interest. High frequency modulation of the light beam is used to determine path length and measure light absorbing compound concentration. Slight shifts in wavelength of the optical sources are used to eliminate interference from scattered light.

Figure 2:
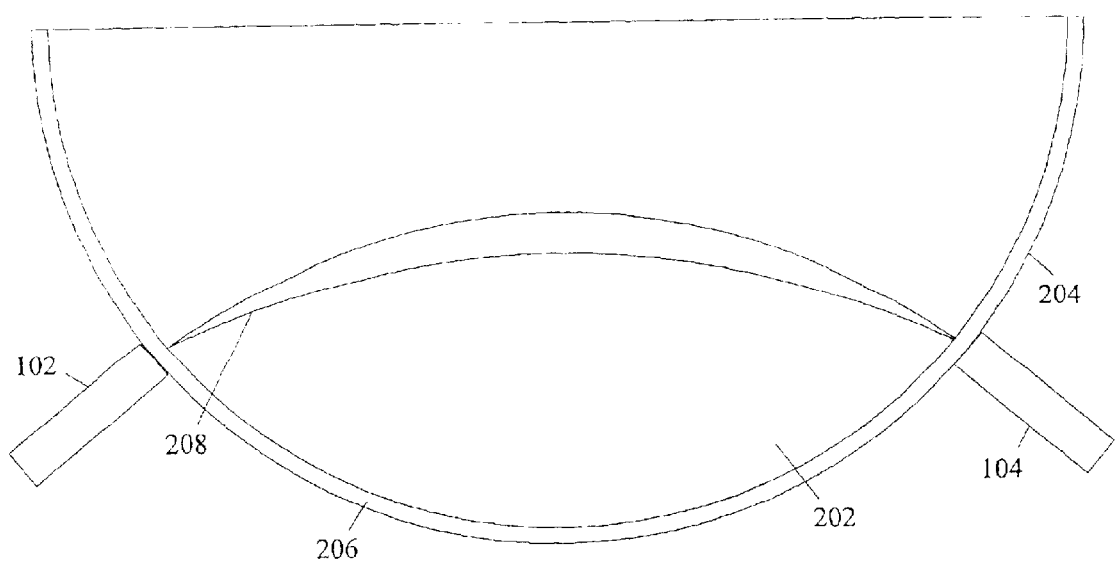
FIG. 2 is a highly schematic pictorial diagram showing an example of a measurement arrangement for measuring light absorbing compounds in biological tissue using a near infrared spectrophotometer.

Referring to FIG. 2 in conjunction with FIG. 1, a highly schematic block diagram shows an example of a measurement arrangement 200 for measuring light absorbing analytes in biological tissue using a near infrared spectrophotometer 100. The measurement arrangement 200 includes the near infrared spectrophotometer 100 configured to measure absorption in cerebral tissue 202. The optical radiation source 102 and the detector 104 are applied to a patient's scalp 204 at appropriate positions on the skull 206 to form an optical path 208 through cerebral tissue 202.

The near infrared spectrophotometer 100 measures the distribution of cerebral light absorbing compounds. The optical source 102 emits near infrared light through the scalp 204 and the skull 206 into cerebral tissue 202. The path of photons that arrive at the detector is a wide arc due to the presence of scatterers in the cerebral tissue 202 that alter the photon trajectory. The detector 104 measures reflected light, which is amplified by amplifier 126 and transmitted via the control interconnections 112 such as a cable.

Near infrared spectrophotometry quantifies the concentration of light absorbing analytes in cerebral tissue 202 by measuring the magnitude of the optical absorption. The Beer-Lambert law states that the optical absorbance of an analyte is proportional to both the concentration of the analyte and the path length. Technical challenges include the difficulty in measuring relatively small absorbances and the difficulty of determining the true optical path length.

The concentration of absorbing analytes in tissue and blood is determined by near infrared spectrophotometry from the difference between the entering light and the reflected light. The differences are caused by light absorption in the analytes and the light scattering effect of tissue in the light path including, for example, scalp and skull as well as soft tissue. Light absorption is described by an absorption coefficient $\mu_a$. Light scattering effect is described by a scattering coefficient $\mu'_s$.

Several different techniques are implemented to ensure accurate measurements. In a first example, wavelengths are selected that reduce or effectively eliminate water interference. In a second example, modulation is used to determine path length. In a third example, a wavelength shift to the entering light is used to eliminate the error caused by the light scattering.

The near infrared spectrophotometer 100 operates at measurement wavelengths at which water does not interfere. Water absorption is weak within the wide 700–900 nm and narrow 1600–1620 nm ranges, allowing clear detection of compounds within the ranges. Light in the wavelength ranges is not absorbed by water and penetrates several centimeters into tissue.

The near infrared spectrophotometer 100 measures pathlength by producing an entering beam that is amplitude modulated with a radio frequency (RF). Phase θ difference of the modulation between the entering light and reflected light is a measure of path length. Phase θ and amplitude A of reflected beam RF modulation are determined with In-Phase (I) and Quadrature (Q) demodulation parameters, according to equations (1) and (2) as follows:

$$\theta = \tan^{-1}\left(\frac{Q_{dc}}{I_{dc}}\right) \quad (1)$$

$$A = \sqrt{Q_{dc}^2 + I_{dc}^2} \quad (2)$$

where the In-Phase (I) and Quadrature (Q) components are produced by the demodulator 124 and used to determine phase difference θ and amplitude A as a measurement of pathlength. In some embodiments, the near infrared spectrophotometer 100 utilizes a controller 114, either internal or external, to measure pathlength.

The near infrared spectrophotometer 100 reduces or eliminates scattering error by varying the entering light wavelength by a few nanometers and then repeating the measurement of the modulation parameters. A slightly different total absorption is obtained because the analyzed absorption coefficients are different for different wavelengths. The scattering coefficient $\mu'_s$ does not change significantly with slight wavelength shift and is therefore a constant. Changes in modulation intensity and phase between the entering and reflected light are related to the absorption coefficient $\mu_a$ by a linear function of c, the speed of light according to equation (3):

$$\mu_a = \frac{\ln 10}{-2c}\left(\frac{\frac{dA}{d\mu_a}}{\frac{d\theta}{d\mu_a}}\right) = \frac{\ln 10}{-2c}\left(\frac{\Delta A}{\Delta \theta}\right) \quad (3)$$

where $dA/d\mu_a$ is the modulation amplitude difference and $d\theta/d\mu_a$ is the phase difference between two slightly shifted wavelengths.

The near infrared spectrophotometer 100 can be used in various clinical applications. In one example, multiple NIRS source-detector pairs are gently held in contact with the scalp by an elastic headband and short-duration measurements, for example 2 second duration, are acquired.

Near infrared spectrophotometry is highly useful for detecting fetal hypoxia The near infrared spectrophotometer 100 is particularly useful for determining the cerebral oxygenation of a fetus during labor and delivery. The measured spectrophotometry value is directly correlated with fetal cerebral oxygenation. The near infrared spectrophotometer optical source and detector are placed on the fetal head and held in place with mild suction when the membrane encasing the fetus is gone and the cervix has dilated about 6 cm. The near infrared spectrophotometer 100 continuously and noninvasively measures cerebral oxygenation throughout labor and delivery. Fetal hypoxia can be detected and alternative clinical procedures, such as Caesarian section, can be initiated if necessary.

The near infrared spectrophotometer 100 can be used to reduce or eliminate unnecessary surgical delivery. An estimated 35% of Caesarian sections performed in the United States are unnecessary because physicians have no reliable way to detect fetal hypoxia. Slight aberrations in Doppler measurement tracings cause some physicians to perform the Caesarian section to avoid lawsuits. Surgical deliveries cost $3000 to $5000, raising the cost of medical care when unnecessary procedures are performed. Furthermore, usage of clinical resources on unnecessary procedures reduces resource available for needed emergency services. For example, injury may result to a child requiring Caesarian delivery if delivery cannot be made quickly due to occupance of the operating room due to unnecessary surgery.

One example of a configuration for measuring absorption in cerebral tissue involves placement of the optical source 102 and detector 104 at recording sites on the left and right frontal-temporal region. Placement is advantageous due to the lack of hair in the region, improving the signal connection with the body. Placement is also advantageous because the brain region is highly involved with cognitive activity.

Arterial Saturation Measurement

One clinical application of near infrared spectrophotometer 100 is measurement of arterial saturation, such as cerebral arterial saturation. The near infrared spectrophotometer 100 performs absorbance measurements at different wavelengths and uses the difference to determine arterial saturation. Saturation values are approximately linearly related to the difference in absorbance values. One or more laser diodes 116 perform measurements at a suitable range of wavelengths. One appropriate wavelength range for arterial saturation measurements using a single laser diode is a range from 795 nm to 805 nm, although other ranges are possible. For the wavelength range from 795 nm to 805 nm, oxyhemoglobin (HbO$_2$) absorbance has a moderate positive slope of +0.01 cm$^{-1}$/nm and deoxyhemoglobin (Hb) absorbance has a negative slope of −0.005 cm$^{-1}$/nm.

In one example of a cerebral arterial saturation measurement, absorbance values are acquired at wavelengths of 799 nm and 801 nm. For 100% saturation the difference between measurements for the two wavelengths is +0.005 cm$^{-1}$. For 0% saturation the difference between measurements for the two wavelengths is −0.0025 cm$^{-1}$.

Near infrared spectrophotometry as disclosed is superior to pulse oximetry for measuring cerebral saturation for several reasons. First, near infrared spectrophotometry accurately quantifies oxygenation and total hemoglobin. Pulse oximeters only measure the ratio of oxygenated hemoglobin to deoxygenated hemoglobin.

Second, near infrared spectrophotometer measurements can be made using only a single optical source. Pulse oximeters require multiple optical sources and multiple optical paths through different regions of tissue. For example one pulse oximeter optical path may extend through an artery while another passes through a vein, potentially resulting in inaccurate oxygenation measurement.

Third, near infrared spectrophotometry can use a single measurement wavelength. Different individuals have different absorbances for Hb and HbO$_2$ at the two different measurement wavelengths. The different absorbances can differ from the experimentally determined constant used in two-source pulse oximeters. One pulse oximeter source may lose output power at a different rate than the other pulse oximeter source, introducing error into the measurement.

Fourth, near infrared spectrophotometry covers the entire range of saturation, from 0% to 100% saturation so that all possible diagnostic conditions can be analyzed. In contrast, pulse oximeters are calibrated with blood samples from volunteers and are limited to a range of about 80–100%.

Fifth, near infrared spectrophotometry is applicable to deep body tissues rather than merely to extremities. For example, near infrared spectrophotometry can be used to measure characteristics and conditions of cerebral tissue. In contrast, pulse oximeters have a very short pathlength and can be used only to measure physiological characteristics in small organs such as a finger or earlobe. Pulse oximetry has little or no utility in conditions such as hemorrhagic shock that severely reduces peripheral vascular flow to extremities such as fingers.

Blood Flow Measurement

Another clinical application of near infrared spectrophotometer 100 is measurement of blood flow, such as cerebral blood flow. The near infrared spectrophotometer 100 accurately measures absorption and determines concentration of deoxyhemoglobin (Hb) and oxyhemoglobin (HbO$_2$) in a selected region of the body. In one example, deoxyhemoglobin and oxyhemoglobin concentration is determined in a selected region of the brain. Cerebral blood flow is the amount of blood passing through a volume of brain tissue and is suitably estimated as the difference between oxygen arrival rate and departure rate from the brain. One accurate estimate of cerebral blood flow is the difference in oxyhemoglobin and deoxyhemoglobin concentrations in the brain, the concentration difference [HbO$_2$]−[Hb].

The near infrared spectrophotometer 100 calculates oxyhemoglobin and deoxyhemoglobin concentrations based on the oxyhemoglobin and deoxyhemoglobin absorption measurements obtained at different wavelengths. In one example of a measurement system, selected wavelengths are 760 nm and 800 nm. At 760 nm, deoxyhemoglobin (Hb) absorption is dominant at a level of approximately 0.08 cm$^{-1}$ in comparison to the oxyhemoglobin (HbO$_2$) absorption of about 0.03 cm$^{-1}$. At 800 nm, oxyhemoglobin (HbO$_2$) absorbance has a positive slope and deoxyhemoglobin (Hb) absorbance has a negative slope. Other wavelengths may be suitable.

In the illustrative embodiment, the near infrared spectrophotometer 100 utilizes controller 114 to perform calculations for solving the two equations for absorption coefficients $\mu_a$ determined at the two wavelengths. The two equations are solved to determine deoxyhemoglobin and oxyhemoglobin concentrations [Hb] and [HbO$_2$], respectively, in equations (4) and (5), as follows:

$$\mu_a^{760} = \varepsilon_{Hb}^{760} \cdot [Hb] + \varepsilon_{HbO2}^{760} \cdot [HbO_2] \qquad (4)$$

and $$\mu_a^{800} = \varepsilon_{Hb}^{800} \cdot [Hb] + \varepsilon_{HbO2}^{800} \cdot [HbO_2] \qquad (5)$$

where $\varepsilon$ are hemoglobin absorption coefficients that are known physical parameters that are specified at various wavelengths included the measurement wavelengths of 760 nm and 800 nm.

The calculation of blood flow is made according to the Fick principle, which states that blood flow, is equal to the metabolic oxygen consumption rate divided by the difference between arterial oxygen and venous oxygen according to equation (6).

$$BloodFlow(ml_{blood}/min) = \frac{O_2 uptake(umol/min)}{(ArterialO_2 - VenousO_2)(umol/mlblood)}. \qquad (6)$$

If oxygen uptake and arterial oxygen are constant, then changes in blood flow produce decreases in venous oxygen. The concentration difference, [HbO2]−[Hb] is highly sensitive to changes in venous oxygen because venous blood makes up approximately 80% of the total cerebral blood volume. Blood flow in a sample volume is determined as the difference between oxyhemoglobin (HbO$_2$) and deoxyhemoglobin (Hb) concentrations according to equation (7), as follows:

$$\text{Blood Flow} = k([HbO_2] - [Hb]) \qquad (7)$$

where k is a constant with units of ml$_{blood}$/min/$\mu$mol.

The near infrared spectrophotometer 100 is superior to other techniques in terms of improved accuracy, lower costs, less complexity, and increased safety.

The near infrared spectrophotometer 100 has increased accuracy fundamentally by a capability to measure both deoxyhemoglobin and oxyhemoglobin concentration in the same body tissue. Aforementioned U.S. Pat. No. 5,251,632 describes a cerebral blood flow measurement apparatus and measurement method that approximate the difference between arterial and venous oxyhemoglobin concentrations using the Fick method by comparing saturation measured by pulse oximetry at a patient's earlobe and saturation measured using near infrared spectrophotometry at the patient's brain. Differences inherent to the two measurement techniques and inherent to physiological characteristics at the two measurement sites reduce the accuracy of the blood flow measurement.

The near infrared spectrophotometer 100 has improved accuracy over other measurement devices and techniques also on the basis that the near infrared spectrophotometer 100 is a self-contained, independent device with full measurement capabilities. Aforementioned U.S. Pat. No. 5,251,632 describes a cerebral blood flow measurement apparatus and measurement method that uses multiple sensor modalities of pulse oximetry and near infrared spectrophotometry, and uses multiple interacting devices including a computer, a gas mixer, a ventilator, and a pulse oximeter in addition to near infrared spectrophotometry. Each of the interacting devices can introduce error into the measurements.

The near infrared spectrophotometer 100 is less complex than other blood flow measurement techniques and devices. As a self-contained, independent device, the near infrared spectrophotometer 100 is capable of simple attachment to the patient without interconnection to any external devices. U.S. Pat. No. 5,251,632 describes a complex system, requiring synchronization of four different medical devices with a computer. The complex system cannot be operated without specially trained staff and software.

The near infrared spectrophotometer 100 reduces expense both in terms of the overall cost of the measurement system and for testing performed using the measurement system. The complex system described in U.S. Pat. No. 5,251,632 requires four different medical devices, a pulse oximeter, a ventilator, a gas mixer, and a near-infrared spectrophotometer, in addition to a computer. Each of the components adds expense. Specially trained staff and software adds to the expense.

The near infrared spectrophotometer 100 increases safety in comparison to blood flow measurement devices and methods. Cerebral blood flow measurements are clinically useful for treating critically ill pre-term infants. These infants can have a high risk of injury resulting from variation in inspired oxygen concentration. Blood measurement techniques that require ventilation present the risk of injury to these infants. Near infrared spectrophotometer 100 is useful for both ventilated and non-ventilated patients.

The near infrared spectrophotometer 100 is highly useful for measuring cerebral blood flow in many clinical settings and situations. Premature Infants are at-risk of developing brain injury resulting from disturbances in cerebral blood flow. Premature infants are susceptible to major fluctuation in mean arterial blood pressure (MAP). Impaired cerebrovascular autoregulation increases the likelihood of changes in MAP that result in germinal matrix-intraventricular hemorrhage (GMH-IVH) and periventricular leukomalacia (PVL). The near infrared spectrophotometer 100 can be used to improve diagnosis of impaired cerebrovascular autoregulation and central nervous system (CNS) hemorrhage in infants and fetuses at the bedside. The near infrared spectrophotometer 100 can also be used to study and define primarily physiologic, but also molecular or cellular, mechanisms that suggest new methods of preventing the sometimes devastating complications of prematurity.

The near infrared spectrophotometer 100 is useful for treating psychological and neurological conditions including schizophrenia, bipolar disorder, and attention deficit/hyperactivity disorder (ADHD). Individuals with schizophrenia and bipolar disorder lack interhemispheric integration of cerebral blood flow found in normal subjects performing cognitive tasks. ADHD children lack cerebral blood flow oscillations in the 0.1–3 Hz range that is common in normal children when they perform cognitive tasks. Cerebral blood flow measurements are also used to monitor medication effects in psychological and neurological conditions.

The near infrared spectrophotometer 100 is capable of acquiring and analyzing bilateral cerebral blood flow measurements in schizophrenic, bipolar and ADHD patients. The near infrared spectrophotometer 100 completes a measurement and records cerebral blood flow rapidly. For example, the near infrared spectrophotometer 100 is capable of completing a measurement in less than two seconds and recording cerebral blood flow every two seconds. Other measurement rates are possible.

The near infrared spectrophotometer 100 is also useful for monitoring cognitive activity and alertness outside a clinical environment. The alertness state of individuals in high-stress occupations such as police work, firefightering, military service, truck driving, and airline piloting can be determined by monitoring cerebral blood flow.

Testing has shown that cerebral blood flow is related to alertness. For example, patients tested using the Wisconsin Card Sorting Test (WCST) show significant increases in cerebral blood flow in the frontal-temporal brain region during testing. In addition, cerebral blood flow increases dramatically just prior to sleep.

Serum Ferritin Measurement

Another area of clinical utility for near infrared spectrophotometer 100 is measurement of serum ferritin. Serum ferritin is a predictor of the acute respiratory distress syndrome (ARDS), a diffuse non-cardiogenic lung edema that kills an estimated 75,000 adults in the USA yearly. ARDS was originally recognized as "shock lung" in battlefield casualties. Presently, no effective treatment for ARDS is known and the personal and economic consequences of ARDS are devastating. ARDS occurs for unknown reasons following a wide variety of predisposing conditions including most predominantly sepsis and/or trauma, and also including blood loss, near drowning, drug reaction, surgery, aspiration, and transfusion. Although the exact pathogenesis of ARDS is unclear, evidence suggests that inflammation involving lung neutrophil accumulation and lung oxidative stress, are contributors to lung leak associated with ARDS. Untreatable clinical problems related to ARDS include acute lung injury (ALI) and multiple organ failure (MOF).

The near infrared spectrophotometer 100 can measure serum ferritin, typically using controller 114 to perform calculations for solving three equations for absorption coefficients $\mu_a$ determined at three wavelengths. Absorption coefficients $\mu_a$ are determined at three wavelengths, for example 760 nm to determine deoxyhemoglobin [Hb] concentration, 800 nm to determine oxyhemoglobin [HbO$_2$] concentration and 850 nm to determine ferritin [Fe+3] concentration. Three equations are solved to determine deoxyhemoglobin, oxyhemoglobin, and ferritin concentrations [Hb], [HbO$_2$], and [Fe+3] concentrations, respectively, in equations (8), (9), and (10), as follows:

$$\mu_a^{760} = \varepsilon_{Hb}^{760} \cdot [Hb] + \varepsilon_{HbO2}^{760} \cdot [HbO_2] + \varepsilon_{Fe+3}^{760} \cdot [Fe+3] \qquad (8)$$

$$\mu_a^{800} = \varepsilon_{Hb}^{800} \cdot [Hb] + \varepsilon_{HbO2}^{800} \cdot [HbO_2] + \varepsilon_{Fe+3}^{800} \cdot [Fe+3] \qquad (9)$$

and $$\mu_a^{850} = \varepsilon_{Hb}^{850} \cdot [Hb] + \varepsilon_{HbO2}^{850} \cdot [HbO_2] + \varepsilon_{Fe+3}^{850} \cdot [Fe+3] \qquad (10)$$

where $\varepsilon$ are hemoglobin and ferritin absorption coefficients that are known physical parameters that are specified at various wavelengths included the measurement wavelengths of 760 nm, 800 nm, and 850 nm.

The near infrared spectrophotometer 100 can be used to noninvasively measure ferritin with or without iron-binding proteins.

Despite evidence that inflammation contributes to acute respiratory distress syndrome, numerous therapies directed at interrupting inflammation mechanisms have all failed to successfully treat established ARDS. For example, clinical trials with steroids, liposomal PGE$_1$, lisofylline, surfactant, and nitric oxide have all shown little benefit as treatments for patients with established ARDS. In all cases, treatment began after ARDS had already developed and, in some cases, these patients had already developed multiple organ failure. Some treatments may be beneficial if therapy begins prior to acute respiratory distress syndrome establishment. Clinical studies show subsets of patents respond favorably to early intervention, when intervention begins prior to the establishments of ARDS. For example, recent reports indicate that treatment with activated protein C may be effective in treating sepsis. The near infrared spectrophotometer 100 can be used to facilitate study of such agents by providing early detection of ARDS by measuring changes in ferritin concentration.

Ferritin has a significant absorbance in the near infrared region and can be measured noninvasively using the near infrared spectrophotometer 100. Ferritin measurements using the near infrared spectrophotometer 100 has several advantages over other ferritin measurements. Typically serum ferritin is measured by blood sampling, requiring a significant waiting period while laboratory testing is performed. The near infrared spectrophotometer 100 can be used to continuously and noninvasively measure ferritin level. The controller 114 monitors the patient for a sudden increase in ferritin level and generates an alarm to the staff so that effective treatment can be applied.

Tissue Blood Gas Measurement

An additional area of clinical utility of the near infrared spectrophotometer 100 is measurement of parameters such as partial pressure of oxygen (PaO$_2$), partial pressure of carbon dioxide (PaCO$_2$), and pH in tissue. The near infrared spectrophotometer 100 is capable of measuring PaCO$_2$, PaO$_2$, and pH noninvasively, for example by using controller 114 to perform calculations for solving three equations for absorption coefficients $\mu_a$ determined at three wavelengths. Absorption coefficients $\mu_a$ are determined at three wavelengths, for example 760 nm to determine deoxyhemoglobin [Hb] concentration, 800 nm to determine oxyhemoglobin [HbO$_2$] concentration, and 1620 nm to determine carbon dioxide [CO$_2$] concentration. Three equations are solved to determine deoxyhemoglobin, oxyhemoglobin, and carbon dioxide concentrations [Hb], [HbO$_2$], and [CO$_2$] concentrations, respectively, in equations (11), (12), and (13), as follows:

$$\mu_a^{760} = \varepsilon_{Hb}^{760} \cdot [Hb] + \varepsilon_{HbO2}^{760} \cdot [HbO_2] + \varepsilon_{CO2}^{760} \cdot [CO_2] \quad (11)$$

$$\mu_a^{800} = \varepsilon_{Hb}^{800} \cdot [Hb] + \varepsilon_{HbO2}^{800} \cdot [HbO_2] + \varepsilon_{CO2}^{800} \cdot [CO_2] \quad (12)$$

and $$\mu_a^{1620} = \varepsilon_{Hb}^{1620} \cdot [Hb] + \varepsilon_{HbO2}^{1620} \cdot [HbO_2] + \varepsilon_{CO2}^{1620} \cdot [CO_2] \quad (13)$$

where $\varepsilon$ are hemoglobin and carbon dioxide absorption coefficients that are known physical parameters that are specified at various wavelengths included the measurement wavelengths of 760 nm, 800 nm, and 1620 nm.

The various parameters, including concentrations of one or more of oxyhemoglobin, deoxyhemoglobin, ferritin, and carbon dioxide, can be measured noninvasively to monitor a patient's condition continuously and without risk of infection, bleeding, blood loss, or invasive procedures. Non-invasive and continuous monitoring has heightened importance in patient's already at-risk because of a medical condition, age, poor veins, and the like.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. An optical sensor comprising:
    an optical source capable of being positioned on a tissue and emitting infrared light into the tissue at a plurality of selected wavelengths;
    a photodetector capable of detecting the selected wavelengths of light from the tissue, the photodetector being positioned on the tissue removed from the optical source but sufficiently close in proximity to the optical source to contact the same general tissue;
    an oscillator coupled to the optical source and providing radio frequency modulation of the optical source, the optical source being responsive to the radio frequency modulation by emitting the plurality of selected wavelengths, the selected wavelengths being selected to generate measurable changes in absorbance of analytes of interest within the tissue; and
    a wavelength modulator coupled to the oscillator and controlling radio frequency modulation of the optical source to emit the plurality of selected wavelengths that are selected to generate the measurable changes in absorbance of analytes of interest within the tissue.

2. An optical sensor according to claim 1 further comprising:
    a demodulator coupled to the photodetector and capable of detecting phase changes of a signal indicative of the radio frequency modulation for the selected wavelengths of light passing through the tissue to measure path length.

3. An optical sensor according to claim 1 further comprising:
    the wavelength modulator being capable of varying the wavelength of the light entering the tissue for a plurality of measurements to reduce scattering errors.

4. An optical sensor according to claim 1 further comprising:
    the wavelength modulator being capable of varying the wavelength of the optical source by varying temperature of the optical source.

5. An optical sensor according to claim 1 further comprising:
    the wavelength modulator being capable of varying the wavelength of the optical source using a micro-electro-mechanical system (MEMS) forming a portion of the optical source.

6. An optical sensor according to claim 1 further comprising:
the wavelength modulator being capable of varying the wavelength of the optical source by varying drive current of the optical source.

7. An apparatus comprising:
a single optical source capable of emitting infrared light into the tissue at a plurality of selected wavelengths;
a detector capable of detecting the selected wavelengths of light in response to emission by the optical source;
an oscillator coupled to the optical source and providing radio frequency modulation of the optical source and wavelength variation of the optical source in the range of ±1% about the selected wavelengths; and
an analyzer coupled to the detector and coupled to the oscillator, the analyzer for analyzing changes in modulation intensity and phase between a signal from the optical source to the detector to measure absorbance of an analyte of interest within the tissue and determine concentration of the analyte according to an equation as follows:

$$\mu_a = \frac{\ln 10}{-2c} \left( \frac{\frac{dA}{d\mu_a}}{\frac{d\theta}{d\mu_a}} \right) = \frac{\ln 10}{-2c} \left( \frac{\Delta A}{\Delta \theta} \right)$$

where $dA/d\mu_a$ is a measured modulation amplitude difference over a slope of absorbance and $d\theta/d\mu_a$ is a measured phase change over the slope of absorbance, the slope of absorbance being defined from known absorbance characteristics of the analyte of interest over the selected wavelength variation range.

8. An apparatus according to claim 7 wherein: the oscillator further comprises:
a power supply; and
a temperature controller.

9. An apparatus according to claim 7 wherein:
the analyzer is a demodulator capable of determining a phase difference θ of modulation between the emitted light and the reflected light and an amplitude A of modulation of the reflected light determined with in-phase and quadrature demodulation parameters.

10. An apparatus according to claim 7 wherein:
the apparatus is a single wavelength pulse oximeter; and
the optical source is a single laser diode with a wavelength range of 760 nm to 850 nm that is wavelength shifted approximately ±2.5 nm, the slope of absorbance between the wavelength-shifted points being equal to a blood oxygen saturation value.

11. An apparatus according to claim 7 wherein: the oscillator further comprises:
a power supply; and
a temperature controller; and
the power supply and temperature controller are capable of activating and modulating the optical source to emit the selected wavelengths in a range of wavelengths within one percent of the first nominal wavelength and to emit the selected wavelengths in a range of wavelengths within one percent of a second nominal wavelength.

12. An apparatus according to claim 11 wherein:
the first nominal wavelength is 760 nm and is modulated between approximately +/−5 nm;
the second nominal wavelength is 800 nm and is modulated between approximately +/−5 nm; and
the first and second wavelengths measure oxyhemoglobin and deoxyhemoglobin concentration in tissue.

13. An apparatus according to claim 12 further comprising:
a processor coupled to the analyzer and capable of noninvasively monitoring oxyhemoglobin and deoxyhemoglobin concentrations in fetal brains, the monitored concentrations being indicative of fetal hypoxia during labor and delivery, the optical source and the detector being capable of attachment to the fetal skull after the mother's membranes break with a low level suction.

14. An apparatus according to claim 12 further comprising:
a processor coupled to the analyzer capable of measuring blood flow as a function of the difference between oxyhemoglobin concentration and deoxyhemoglobin concentration, the apparatus measuring blood flow noninvasively.

15. An apparatus according to claim 12 further comprising:
a processor coupled to the analyzer capable of noninvasively measuring the concentrations so that measurements are made continuously and without risk of infection, bleeding, blood loss, or invasive procurement procedures.

16. An apparatus according to claim 7 wherein:
the oscillator is capable of activating and modulating the optical source to emit the selected wavelengths in a range of wavelengths with one percent of the first nominal wavelength, emit the selected wavelengths in a range of wavelengths within one percent of a second nominal wavelength, and emit the selected wavelengths in a range of wavelengths within one percent of a third nominal wavelength.

17. An apparatus according to claim 16 wherein:
the first nominal wavelength is 760 nm and is modulated between approximately +/−5 nm;
the second nominal wavelength is 800 nm and is modulated between approximately +/−5 nm;
the third nominal wavelength is 850 nm and is modulated between approximately +/−5 nm; and
the first, second, and third wavelengths measure oxyhemoglobin, deoxyhemoglobin, and ferritin concentrations in tissue.

18. An apparatus according to claim 17 further comprising:
a processor coupled to the analyzer capable of predicting patients at risk for acute respiratory distress syndrome that will progress to acute respiratory distress syndrome based on measurement of changes in ferritin concentration.

19. An apparatus according to claim 17 further comprising:
a processor coupled to the analyzer capable of monitoring medication effects in acute respiratory distress syndrome patients.

20. An apparatus according to claim 17 further comprising:
a processor coupled to the analyzer capable of noninvasively measuring ferritin concentration with or without iron-binding proteins.

21. An apparatus according to claim 16 wherein:
the first nominal wavelength is 760 nm and is modulated between approximately +/−5 nm;

the second nominal wavelength is 800 nm and is modulated between approximately +/−5 nm;

the third nominal wavelength is 1620 nm and is modulated between approximately +/−10 nm; and the first, second, and third wavelengths measure oxyhemoglobin, deoxyhemoglobin, and carbon dioxide concentrations in tissue.

22. An apparatus according to claim 21 wherein:

the apparatus is capable of measuring oxyhemoglobin, deoxyhemoglobin, and carbon dioxide concentration noninvasively in tissue.

23. An apparatus according to claim 7 wherein:

the oscillator is capable of activating and modulating the optical source to emit the selected wavelengths in a range of wavelengths within one percent of the first nominal wavelength, emit the selected wavelengths in a range of wavelengths within one percent of a second nominal wavelength, emit the selected wavelengths in a range of wavelengths within one percent of a third nominal wavelength, and emit the selected wavelength in a range of wavelengths within one percent of a fourth nominal wavelength.

24. An apparatus according to claim 23 wherein:

the first nominal wavelength is 760 nm and is modulated between approximately +/−5 nm;

the second nominal wavelength is 800 nm and is modulated between approximately +/−5 nm;

the third nominal wavelength is 850 nm and is modulated between approximately +/−5 nm; and the fourth nominal wavelength is 1620 nm and is modulated between approximately +/−10 nm.

25. An apparatus according to claim 24 wherein:

the first, second, third, and fourth wavelengths measure oxyhemoglobin, deoxyhemoglobin, ferritin, and carbon dioxide concentration in tissue.

26. An apparatus according to claim 25 further comprising:

a processor coupled to the analyzer capable of noninvasively measuring the concentrations so that measurements are made continuously and without risk of infection, bleeding, blood loss, or invasive procurement procedures.

27. An apparatus according to claim 25 further comprising:

a processor coupled to the analyzer capable of measuring oxyhemoglobin, deoxyhemoglobin, ferritin, and carbon dioxide concentration for improving diagnosis, treatment including specificity and dosing, or prevention of a pathophysiologic condition.

28. An apparatus according to claim 27 further comprising:

a processor including a process for monitoring of exercise, aging, and related physiologic functions.

29. An apparatus according to claim 25 further comprising:

a process executable in the processor capable of monitoring a condition and managing application of medication based on the monitoring.

30. An apparatus according to claim 25 further comprising:

a process executable in the processor capable of monitoring a condition and managing automated application of inspired oxygen levels to minimal oxygen level requirements of a patient to supply effective oxygenation based on the monitoring.

31. An apparatus according to claim 25 further comprising:

a process executable in the processor capable of measuring oxygen concentration in conditions of patients who are supplemented with additional concentrations of oxygen.

32. An apparatus according to claim 25 further comprising:

a process executable in the processor capable of assessing perfusion following surgery or organ transplantation.

33. An apparatus according to claim 25 further comprising:

a process executable in the processor capable of diagnosing stroke, transient ischemic attack, atherosclerosis, and anemia.

34. An optical sensor comprising:

means positionable on a tissue for emitting near infrared light into the tissue at a plurality of selected wavelengths;

means for detecting reflected light from the tissue, the means for detecting being positioned on the tissue removed from the emitting means but sufficiently close in proximity to the emitting means to contact the same general tissue;

means for activating the optical source to emit the near infrared light; and means for controlling oscillation of the emitting means to emit a plurality of wavelengths that are selected to vary absorption amplitude and slope of a compound of interest within the tissue.

35. An optical sensor according to claim 34 wherein:

the means for controlling oscillation is a means for controlling power and temperature of the emitting means.

* * * * *